(12) United States Patent
Brown et al.

(10) Patent No.: US 7,939,556 B2
(45) Date of Patent: May 10, 2011

(54) IMIDAZOLE DERIVATIVES AND THEIR USE FOR MODULATING THE GABA$_A$ RECEPTOR COMPLEX

(75) Inventors: William Dalby Brown, Søborg (DK); Janus S. Larsen, Holbæk (DK); Lene Teuber, Værløse (DK); David Tristram Brown, Albertslund (DK); Philip K. Ahring, Bagsværd (DK); Naheed Mirza, Birkerød (DK); Elsebet Østergaard Nielsen, København K (DK)

(73) Assignee: Neurosearch A/S, Ballerup (DK)

( * ) Notice: Subject to any disclaimer, the term of this patent is extended or adjusted under 35 U.S.C. 154(b) by 240 days.

(21) Appl. No.: 12/089,883

(22) PCT Filed: Oct. 12, 2006

(86) PCT No.: PCT/EP2006/067314
§ 371 (c)(1),
(2), (4) Date: Aug. 20, 2008

(87) PCT Pub. No.: WO2007/042545
PCT Pub. Date: Apr. 19, 2007

(65) Prior Publication Data
US 2009/0209597 A1    Aug. 20, 2009

Related U.S. Application Data

(60) Provisional application No. 60/726,678, filed on Oct. 17, 2005.

(30) Foreign Application Priority Data

Oct. 14, 2005 (DK) ................................. 2005 01444

(51) Int. Cl.
*A61K 31/415* (2006.01)

(52) U.S. Cl. ...................... 514/400; 514/341; 548/334.5; 546/275.1

(58) Field of Classification Search ............... 548/311.1, 548/333.5, 334.5; 514/397, 399, 400, 341; 546/275.1
See application file for complete search history.

(56) References Cited

U.S. PATENT DOCUMENTS

| | | | | |
|---|---|---|---|---|
| 4,952,698 A | * | 8/1990 | Biere et al. | 548/131 |
| 5,179,111 A | * | 1/1993 | Biere et al. | 514/341 |
| 6,683,097 B2 | * | 1/2004 | Alanine et al. | 514/341 |
| 6,936,613 B2 | * | 8/2005 | Teuber et al. | 514/252.19 |

FOREIGN PATENT DOCUMENTS

| | | |
|---|---|---|
| EP | 0 323 799 A1 | 7/1989 |
| WO | WO-88/01268 A1 | 2/1988 |
| WO | WO-96/07645 A1 | 3/1996 |
| WO | WO-00/78728 A1 | 12/2000 |
| WO | WO-02/060877 A1 | 8/2002 |

OTHER PUBLICATIONS

Asproni, Battistina et al., Journal of Medicinal Chemistry, 48 (7), Apr. 7, 2005, pp. 2638-2645.
International Preliminary Report on Patentability issued Apr. 15, 2008, in PCT/EP2006/067314.

* cited by examiner

*Primary Examiner* — Yong Chu
*Assistant Examiner* — Valerie Rodriguez-Garcia
(74) *Attorney, Agent, or Firm* — Birch, Stewart, Kolasch & Birch, LLP

(57) ABSTRACT

This invention relates to novel imidazole derivatives, pharmaceutical compositions containing these compounds, and methods of treatment therewith.
The compounds of the invention are useful in the treatment of central nervous system diseases and disorders, which are responsive to modulation of the GABA$_A$ receptor complex, and in particular for combating anxiety and related diseases.

7 Claims, No Drawings

IMIDAZOLE DERIVATIVES AND THEIR USE FOR MODULATING THE GABA$_A$ RECEPTOR COMPLEX

This application is the National Phase of PCT/EP2006/067314 filed on Oct. 12, 2006, which claims priority under 35 U.S.C. 119(e) to U.S. Provisional Application No. 60/726,678 filed on Oct. 17, 2005 and under 35 U.S.C. 119(a) to Patent Application No. PA 2005 01444 filed in Denmark on Oct. 14, 2005. Both of these prior applications are hereby expressly incorporated by reference into the present application.

TECHNICAL FIELD

This invention relates to novel imidazole derivatives, pharmaceutical compositions containing these compounds, and methods of treatment therewith.

The compounds of the invention are useful in the treatment of central nervous system diseases and disorders, which are responsive to modulation of the GABA$_A$ receptor complex, and in particular for combating anxiety and related diseases.

BACKGROUND ART

The modulatory sites on the GABA$_A$ receptor complex, such as for example the benzodiazepine binding site, are the targets for anxiolytic drugs, such as the classical anxiolytic benzodiazepines. However, they are associated with a number of undesirable features.

Multiple isoforms of the GABA$_A$ receptor exist; each receptor is a pentameric complex comprising subunits drawn from $\alpha_{1-6}$, $\beta_{1-3}$, $\gamma_{1-3}$, $\delta$, $\epsilon$, and $\theta$ subunit isoforms. The classical anxiolytic benzodiazepines show no subtype selectivity. It has been suggested that one of the key elements in the disadvantages of the classical benzodiazepanes (such as sedation, dependency and cognitive impairment) is relates to the $\alpha$1 subunit of the GABA$_A$ receptors. Thus compounds with selectivity for the $\alpha$2 and/or $\alpha$3 subunits over the $\alpha$1 subunit are expected to have an improved side effect profile.

Thus, there is still a strong need for compounds with an optimised pharmacological profile. Furthermore, there is a strong need to find effective compounds without unwanted side effects associated with older compounds.

SUMMARY OF THE INVENTION

In its first aspect, the invention provides a compound of Formula I:

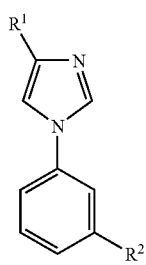

(I)

any of its isomers or any mixture of its isomers, or a pharmaceutically acceptable salt thereof,
wherein R$^1$ and R$^2$ are defined as below.

In its second aspect, the invention provides a pharmaceutical composition, 6 comprising a therapeutically effective amount of a compound of the invention, any of its isomers or any mixture of its isomers, or a pharmaceutically acceptable salt thereof, together with at least one pharmaceutically acceptable carrier, excipient or diluent.

In a further aspect, the invention provides the use of a compound of the invention, any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the GABA$_A$ receptor complex in the central nervous system.

In a still further aspect, the invention relates to a method for treatment, prevention or alleviation of a disease or a disorder or a condition of a living animal body, including a human, which disorder, disease or condition is responsive to modulation of the GABA$_A$ receptor complex in the central nervous system, which method comprises the step of administering to such a living animal body in need thereof a therapeutically effective amount of a compound of the invention, any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Imidazole Derivatives

In its first aspect the present invention provides a compound of the general formula (I):

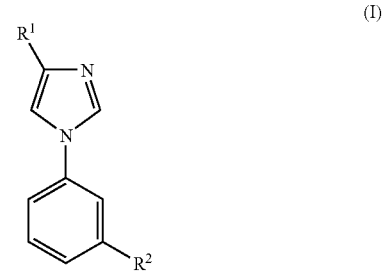

(I)

any of its isomers or any mixture of its isomers,
or a pharmaceutically acceptable salt thereof,
wherein
R$^1$ represents —COOR$^3$;
  wherein R$^3$ represents hydrogen, alkyl, cycloalkyl, cycloalkylakyl, alkenyl, alkynyl, aryl or heteroaryl;
    which aryl or heteroaryl group is optionally substituted with one or more substituents independently selected from the group consisting of:
      halo, hydroxy, R$^a$R$^b$N—, R$^a$R$^b$N-alkyl, cyano, nitro, trifluoromethyl, trifluoromethoxy, alkoxy, cycloalkoxy, R$^a$—(C=O)—, R$^a$—O—(C=O)—, alkyl, cycloalkyl, cycloalkylalkyl, alkenyl, and alkynyl;
        wherein R$^a$ and R$^b$ independent of each other are hydrogen or alkyl;
R$^2$ represents
  halo, nitro, R$^c$— or R$^c$—(CH$_2$)$_m$—O—(CH$_2$)$_n$—;
  wherein m is 0 or 1; n is 0 or 1; and $R^c$ is an aryl or heteroaryl group;
which aryl or heteroaryl group is optionally substituted with one or more substituents independently selected from the group consisting of:
halo, hydroxy, $R^dR^eN$—, $R^dR^eN$-alkyl, $R^dR^eN$—(C=O)—, cyano, nitro, trifluoromethyl, trifluoromethoxy, alkoxy, cycloalkoxy, $R^d$—(C=O)—, $R^d$—O—(C=O)—, alkyl, cycloalkyl, cycloalkylalkyl, alkenyl, and alkynyl;
wherein $R^d$ and $R^e$ independent of each other are hydrogen or alkyl.

In one embodiment, $R^1$ represents —COOR$^3$; wherein $R^3$ represents hydrogen or alkyl. In a special embodiment, $R^3$ represents hydrogen. In a further embodiment, $R^3$ represents alkyl, such as methyl, ethyl or butyl, such as n-butyl.

In a further embodiment, $R^1$ represents —COOR$^3$; wherein $R^3$ represents heteroaryl. In a special embodiment, $R^3$ represents pyridyl, such as pyridin-3-yl.

In a still further embodiment, $R^2$ represents halo or nitro. In a special embodiment, $R^2$ represents halo such as bromo. In a further embodiment, $R^2$ represents nitro.

In a further embodiment, $R^2$ represents $R^c$ or $R^c$—(CH$_2$)$_m$—O—(CH$_2$)$_n$—;
wherein m is 0 or 1; n is 0 or 1; and
$R^c$ is an aryl or heteroaryl group;
which aryl or heteroaryl group is optionally substituted with one or more substituents independently selected from the group consisting of:
halo, hydroxy, $R^dR^eN$—, $R^dR^eN$-alkyl, $R^dR^eN$—(C=O)—, cyano, nitro, trifluoromethyl, trifluoromethoxy, alkoxy, cycloalkoxy, $R^d$—(C=O)—, $R^d$—O—(C=O)—, alkyl, cycloalkyl, cycloalkylalkyl, alkenyl, and alkynyl;
wherein $R^d$ and $R^e$ independent of each other are hydrogen or alkyl.

In a special embodiment, $R^2$ represents $R^c$, wherein $R^c$ is an optionally substituted aryl, such as phenyl. In a further embodiment, $R^2$ represents alkoxy-halo-phenyl, such as methoxy-fluoro-phenyl, such as 3-fluoro-2-methoxy-phenyl 5-fluoro-2-methoxy-phenyl or 6-fluoro-2-methoxy-phenyl. In a still further embodiment, $R^2$ represents alkoxy-phenyl, such as methoxy-phenyl, such as 2-methoxy-phenyl. In a further embodiment, $R^2$ represents cyano-phenyl, such as 2-cyano-phenyl. In a still further embodiment, $R^2$ represents halo-phenyl, such as chloro-phenyl, such as 2-chloro-phenyl. In a further embodiment, $R^2$ represents trifluoromethoxy-phenyl, such as 2-trifluoromethoxy-phenyl.

In a further embodiment, $R^2$ represents $R^c$, wherein $R^c$ is an optionally substituted heteroaryl, such as an optionally substituted pyridyl. In a special embodiment, $R^2$ represents halopyridyl, such as fluoropyridyl or chloropyridyl, such as 6-fluoro-pyridin-3-yl, 2-fluoropyridin-3-yl, 2-fluoropyridin-4-yl and 2-chloropyridin-3-yl. In a further embodiment, $R^2$ represents dihalopyridyl, such as difluoropyridyl, such as 2,4-difluoropyridin-3-yl. In a still further embodiment, $R^2$ represents dialkoxypyridyl, such as dimethoxypyridyl, such as 2,4-dimethoxypyridin-5-yl.

In a still further embodiment, $R^2$ represents $R^c$—(CH$_2$)$_m$—O—(CH$_2$)$_n$—; wherein m is 1; n is 1; and $R^c$ is an optionally substituted heteroaryl, such as an optionally substituted pyridyl or an optionally substituted imidazol. In a special embodiment, $R^c$ is pyridyl, such as pyridin-2-yl. In a further embodiment, $R^c$ is alkylimidazolyl, such as methylimidazolyl, such as 1-methyl-H-imidazoly-2-yl.

In a special embodiment the chemical compound of the invention is
1-[3-(Pyridin-2-ylmethoxymethyl)-phenyl]-1H-imidazole-4-carboxylic acid ethyl ester;
1-[3-(1-Methyl-1H-imidazol-2-ylmethoxymethyl)-phenyl]-1H-imidazole-4-carboxylic acid ethyl ester;
1-(3-Bromo-phenyl)-1H-imidazole-4-carboxylic acid ethyl ester;
1-(3-Bromo-phenyl)-1H-imidazole-4-carboxylic acid n-butyl ester;
1-Biphenyl-3-yl-1H-imidazole-4-carboxylic acid ethyl ester hydrochloride;
1-[3-(6-Fluoro-pyridin-3-yl)-phenyl]-1H-imidazole-4-carboxylic acid ethyl ester;
1-(3-Nitro-phenyl)-1H-imidazole-4-carboxylic acid methyl ester;
1-(3-Nitro-phenyl)-1H-imidazole-4-carboxylic acid;
1-(3-Nitro-phenyl)-1H-imidazole-4-carboxylic acid pyridin-3-yl ester;
1-(3-Bromo-phenyl)-1H-imidazole-4-carboxylic acid pyridin-3-yl ester;
1-(5'-Fluoro-2'-methoxy-biphenyl-3-yl)-1H-imidazole-4-carboxylic acid ethyl ester;
1-(2'-Methoxy-biphenyl-3-yl)-1H-imidazole-4-carboxylic acid ethyl ester;
1-(2'-Cyano-biphenyl-3-yl)-1H-imidazole-4-carboxylic acid ethyl ester;
1-(2'-Chloro-biphenyl-3-yl)-1H-imidazole-4-carboxylic acid ethyl ester;
1-(2'-Trifluoromethoxy-biphenyl-3-yl)-1H-imidazole-4-carboxylic acid ethyl ester;
1-(6'-Fluoro-2'-methoxy-biphenyl-3-yl)-1H-imidazole-4-carboxylic acid ethyl ester;
1-(3'-Fluoro-2'-methoxy-biphenyl-3-yl)-1H-imidazole-4-carboxylic acid ethyl ester;
1-[3-(2-Fluoro-pyridin-3-yl)-phenyl]-1H-imidazole-4-carboxylic acid ethyl ester;
1-[3-(2,4-Difluoro-pyridin-3-yl)-phenyl]-1H-imidazole-4-carboxylic acid ethyl ester;
1-[3-(2-Fluoro-pyridin-4-yl)-phenyl]-1H-imidazole-4-carboxylic acid ethyl ester;
1-[3-(2-Chloro-pyridin-3-yl)-phenyl]-1H-imidazole-4-carboxylic acid ethyl ester;
1-[3-(2,4-Dimethoxy-pyrimidin-5-yl)-phenyl]-1H-imidazole-4-carboxylic acid ethyl ester;
1-Biphenyl-3-yl-1H-imidazole-4-carboxylic acid;
1-(5'-Fluoro-2'-methoxy-biphenyl-3-yl)-1H-imidazole-4-carboxylic acid;
1-(2'-Methoxy-biphenyl-3-yl)-1H-imidazole-4-carboxylic acid;
1-(2'-Cyano-biphenyl-3-yl)-1H-imidazole-4-carboxylic acid;
1-(2'-Chloro-biphenyl-3-yl)-1H-imidazole-4-carboxylic acid;
1-(2'-Trifluoromethoxy-biphenyl-3-yl)-1H-imidazole-4-carboxylic acid;
1-(6'-Fluoro-2'-methoxy-biphenyl-3-yl)-1H-imidazole-4-carboxylic acid;
1-(3'-Fluoro-2'-methoxy-biphenyl-3-yl)-1H-imidazole-4-carboxylic acid;
1-[3-(2-Fluoro-pyridin-3-yl)-phenyl]-1H-imidazole-4-carboxylic acid;
1-[3-(2,4-Difluoro-pyridin-3-yl)-phenyl]-1H-imidazole-4-carboxylic acid;
1-[3-(2-Fluoro-pyridin-4-yl)-phenyl]-1H-imidazole-4-carboxylic acid;

1-[3-(2-Chloro-pyridin-3-yl)-phenyl]-1H-imidazole-4-carboxylic acid;
1-[3-(2,4-Dimethoxy-pyrimidin-5-yl)-phenyl]-1H-imidazole-4-carboxylic acid;
any of its isomers or any mixture of its isomers,
or a pharmaceutically acceptable salt thereof.

Any combination of two or more of the embodiments as described above is considered within the scope of the present invention.

DEFINITION OF SUBSTITUENTS

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butadienyl; 1-, 2-, 3-, 4- or 5-hexenyl, or 1,3-hexadienyl, or 1,3,5-hexatrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-henynyl, or 1,3-hexadiynyl or 1,3,5-hexatriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy means O-alkyl, wherein alkyl is as defined above.

Alkoxyalkyl means alkoxy as above and alkyl as above, meaning for example, methoxymethyl.

In the context of this invention an aryl group designates a carbocyclic aromatic ring system such as phenyl, naphthyl (1-naphthyl or 2-naphthyl) or fluorenyl.

In the context of this invention a heteroaryl group designates an aromatic mono- or bicyclic heterocydic group, which holds one or more heteroatoms in its ring structure. Preferred heteroatoms include nitrogen (N), oxygen (O), and sulphur (S).

Preferred monocyclic heteroaryl groups of the invention include aromatic 5- and 6-membered heterocyclic monocyclic groups, including for example, but not limited to, oxazolyl, isoxazolyl, thiazolyl, isothiazolyl, tetrazolyl, 1,2,4-oxadiazolyl, 1,2,5-oxadiazolyl, 1,3,4-oxadiazolyl, triazolyl, 1,2,4-thiadiazolyl, 1,2,5-thiadiazolyl, imidazolyl, pyrrolyl, pyrazolyl, furanyl, thienyl, pyridyl, pyrimidyl, pyridazinyl or pyrazinyl.

Preferred bicyclic heteroaryl groups of the invention include for example, but not limited to, indolizinyl, indolyl, isoindolyl, indazolyl, benzofuranyl, benzo[b]thienyl, benzimidazolyl, benzoxazolyl, benzooxadiazolyl, benzothiazolyl, benzo[d]isothiazolyl, purinyl, quinolinyl, isoquinolinyl, cinnolinyl, phthalazinyl, quinazolinyl, quinoxalinyl, 1,8-naphthyridinyl, pteridinyl, and indenyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable add addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may exist in different stereoisomeric forms—including enantiomers, diastereomers and cis-trans-isomers.

The invention includes all such isomers and any mixtures thereof including racemic mixtures.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2H$ (deuterium), $^3H$ (tritium), $^{13}C$, $^{14}C$, $^{131}I$, $^{125}I$, $^{123}I$, and $^{18}F$.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Biological Activity

Compounds of the invention are capable of modulating the $GABA_A$ receptor complex. They may be tested for their ability to bind to the $GABA_A$ receptor complex, including specific subunits thereof.

The compounds of the present invention, being ligands for the benzodiazepine binding site on $GABA_A$ receptors, are therefore of use in the treatment and/or prevention of a variety of disorders of the central nervous system. Thus in further aspect, the compounds of the invention are considered useful for the treatment, prevention or alleviation of a disease, disorder or condition responsive to modulation of the $GABA_A$ receptor complex in the central nervous system.

In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

stress disorders including post-traumatic and acute stress disorder;

sleep disorders;

memory disorder;

neuroses;

convulsive disorders, for example epilepsy, seizures, convulsions, or febrile convulsions in children;

migraine;

mood disorders;

depressive or bipolar disorders, for example depression, single-episode or recurrent major depressive disorder, dysthymic disorder, bipolar disorder, bipolar I and bipolar II manic disorders, and cyclothymic disorder, psychotic disorders, including schizophrenia;

neurodegeneration arising from cerebral ischemia;

attention deficit hyperactivity disorder;

pain and nociception, e.g. neuropathic pain;

emesis, including acute, delayed and anticipatory emesis, in particular emesis induced by chemotherapy or radiation;

motion sickness, post-operative nausea and vomiting;

eating disorders including anorexia nervosa and bulimia nervosa;

premenstrual syndrome;

neuralgia, e.g. trigeminal neuralgia;

muscle spasm or spasticity, e.g. in paraplegic patients;

the effects of substance abuse or dependency, including alcohol withdrawal;

cognitive disorders, such as Alzheimer's disease;

cerebral ischemia, stroke, head trauma;

tinnitus: and disorders of circadian rhythm, e.g. in subjects suffering from the effects of jet lag or shift work.

Preferably the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

Further, the compounds of the invention may be useful as radioligands in assays for detecting compounds capable of binding to the human $GABA_A$ receptor.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the $GABA_A$ receptor complex in the central nervous system, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge. When administered in combination with compounds known in the art for treatment of the diseases, the doses regimen may be reduced.

EXAMPLES

The invention is further illustrated with reference to the following examples, which are not intended to be in any way limiting to the scope of the invention as claimed.

Example 1

The synthesis of intermediate compound 7 is shown in Scheme 1:

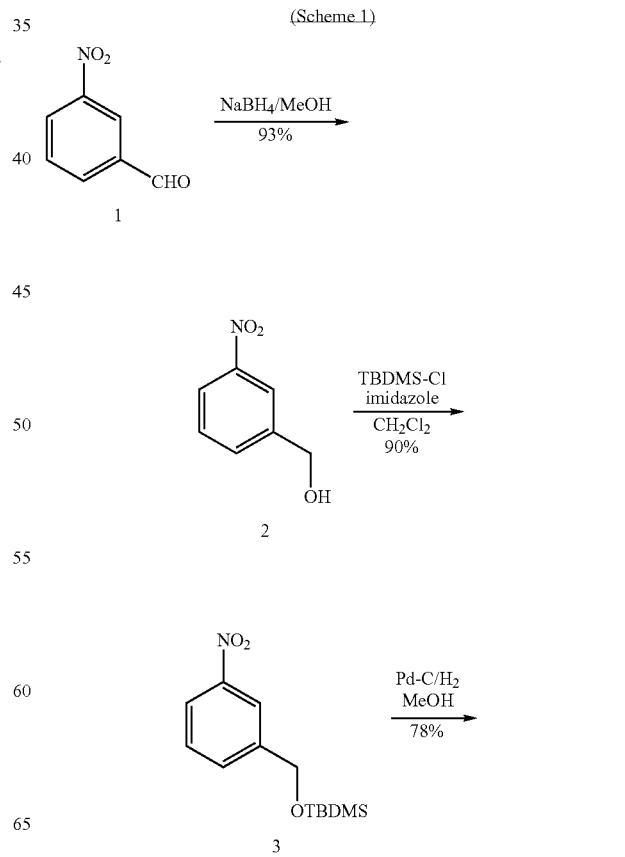

-continued

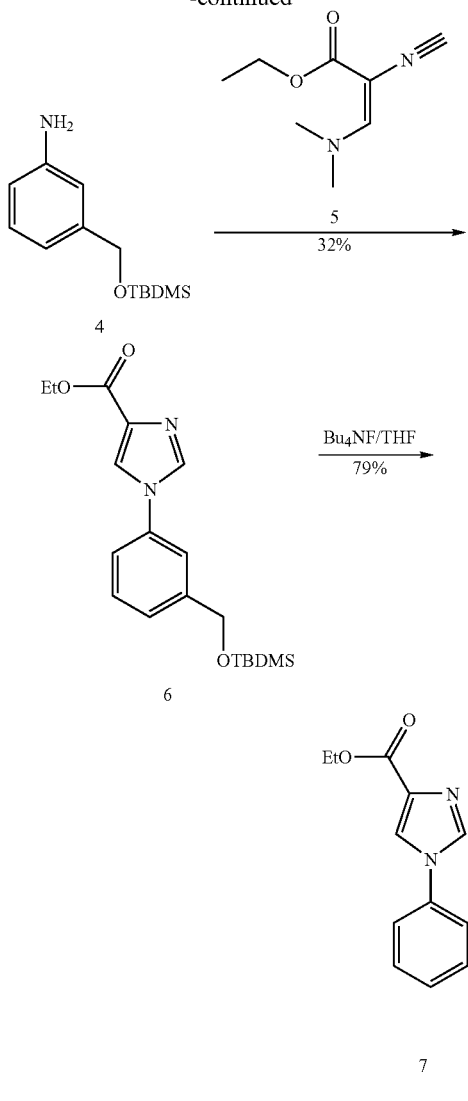

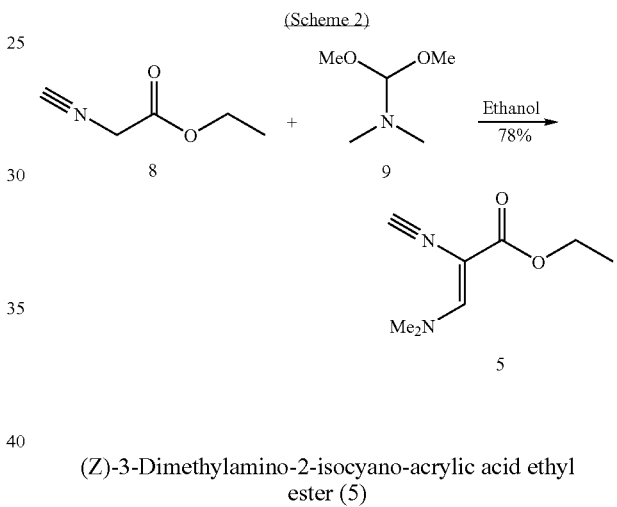

(Z)-3-Dimethylamino-2-isocyano-acrylic acid ethyl ester (5)

(3-Nitro-phenyl)-methanol (2)

To a solution of 3-nitrobenzaldehyde (1) (200 g, 1.32 mol) in methanol (1000 mL) at 0° C. under $N_2$ atmosphere was slowly added $NaBH_4$ (25 g, 0.66 mol) and then the reaction mixture was allowed to stir at room temperature for 1 h. The reaction mixture was re-cooled to 0° C. and quenched with ice-water, methanol was removed under reduced pressure and the residue was extracted with $CH_2Cl_2$ (5×200 mL). The combined organic layer was washed with brine, dried over anhydrous $Na_2SO_4$ and concentrated to furnish compound 2 (190.7 g, 93%) as liquid which was taken as such for next step.

tert-Butyl-dimethyl-(3-nitro-benzyloxy)-silane (3)

A solution of compound 2 (4.7 g, 0.03 mol) and imidazole (2.71 g, 0.04 mol) in dry $CH_2Cl_2$ (30 mL) under $N_2$ atmosphere at 0° C. was added a solution of TBDMS-Cl (5.08 g, 0.033 mol) in $CH_2Cl_2$ (15 mL) and allowed to stir at room temperature for 2 h. The precipitated solid was isolated by filtration and washed with $CH_2Cl_2$ (5×20 mL). The filtrate and combined $CH_2Cl_2$ fractions were dried over anhydrous $Na_2SO_4$ and concentrated under reduced pressure. The crude mass was purified by column chromatography (silica gel, eluant=3:7 mixture of ethyl acetate and hexane) to afford compound 3 (7.2 g, 90%) as a liquid.

3-tert-Butyl-dimethyl-silanyloxymethyl)-phenylamine (4)

A solution of compound 3 (7.2 g, 0.027 mol) in dry methanol (40 mL) was hydrogenated using Pd/C (0.72 g, 100% Pd on carbon) as catalyst under 2 Kg of pressure for 3 h. The reaction mixture was filtered through celite, washed with methanol and the combined organic solvent was concentrated under reduced pressure to give compound 4 (5.0 g, 78%) as liquid which was taken as such for next step.

Example 2

The synthesis of intermediate compound 5 is shown in Scheme 2 (Modified from *Org. Lett.* 2002, 4, 4133):

To a solution of ethyl iso-cyanoacetate (8) (10 g, 88.4 mmol) in absolute ethanol (100 mL) at 0° C. under $N_2$ atmosphere was added dimethoxymethyl dimethyl-amine (9) (23.4 mL, 176.8 mmol.) dropwise while stirring was continued at room temperature for 12 h. The reaction mixture was concentrated under reduced pressure to remove ethanol. The residue (crude mass, brown color) was purified by column chromatography over neutral alumina using 3 to 4% ethyl acetate in hexane as eluant. Solvent fractions were concentrated under reduced pressure and low temperature (to avoid polymerization of compound) to furnish compound 5 (11.6 g, 78%) as pale orange liquid which was solidified on cooling at 4° C.

[1-[3-(tert-Butyl-dimethyl-silanyloxymethyl)-phenyl]-1H-imidazole-4-carboxylic acid ethyl ester] (6)

A mixture of compound 4 (4.2 g, 17.7 mmol) and compound 5 (2.5 g, 14.77 mmol) in butanol (10 mL) was heated at 120° C. for 2 days. The reaction mixture was allowed to cool to room temperature, concentrated and purified by column chromatography using 30% ethylacetate in hexane to furnish imidazole 6 (1.7 g, 32%) as a colorless oil.

[1-(3-Hydroxymethyl-phenyl)-1H-imidazole-4-carboxylic acid ethyl ester] (7)

To a solution of compound 6 (1.50 g, 4.2 mmol) in THF (18 mL) was added tetrabutylammonium fluoride (1.58 g, 5 mmol) and refluxed at 70° C. for 12 h. After concentration, the residue was purified by filter column using 4% methanol in chloroform to give alcohol 7 (810 mg, 79%) as pale yellow gum.

Example 3

The synthesis of compound 11a is shown in Scheme 3:

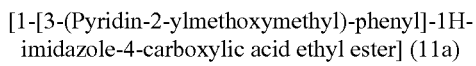

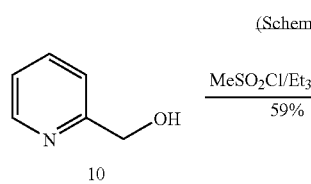

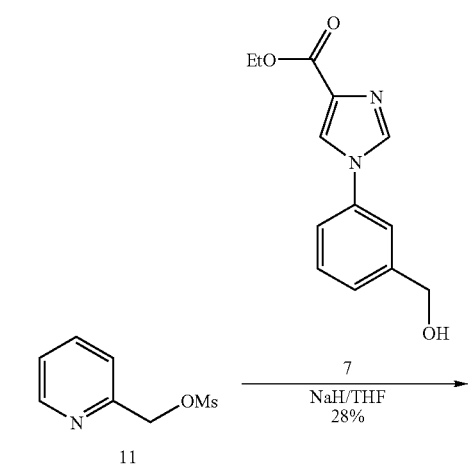

[Methanesulfonic acid pyridin-2-ylmethyl ester] (11)

To a solution of 2-pyridylcarbinol (10) (300 mg, 2.70 mmol) and triethyl amine (698 mg, 6.75 mmol) in dry THF (10 mL) at 0° C. was added a solution of mesylchloride (470 mg, 4.1 mmol) in dry THF (10 mL). Reaction mixture was allowed to stir for 2 h at room temperature [reaction was followed by TLC]. Reaction mixture was concentrated to remove THF under reduced pressure and the residue was dissolved in CH$_2$Cl$_2$ (100 mL), washed with brine, dried over anhydrous Na$_2$SO$_4$ and concentrated under reduced pressure to give compound 11 (300 mg, 59%) as gum and it was taken as such for next step.

[1-[3-(Pyridin-2-ylmethoxymethyl)-phenyl]-1H-imidazole-4-carboxylic acid ethyl ester] (11a)

To a suspension of NaH (120 mg, 3 mmol, 60% in mineral oil) in dry THF (10 mL) at 0° C. under N$_2$ atmosphere was added a solution of compound 7 (394 mg, 1.2 mmol) in dry THF (5 mL) and reaction mixture was allowed to stir for 30 min at room temperature. Compound 11 (300 mg, 1.2 mmol) in THF (2 mL) was then added and stirring was continued for 12 h at room temperature [reaction was followed by TLC]. Reaction mixture was quenched with water (5 mL), extracted with CH$_2$Cl$_2$ (40 mL), washed with brine, dried over Na$_2$SO$_4$ and concentrated. The crude mass was purified by column chromatography over silica gel using 10% methanol in chloroform as eluant to give 11a (110 mg, 28%) as pale yellow solid, mp 76.7-78.8° C.

Example 4

The synthesis of compound 14a is shown in Scheme 4:

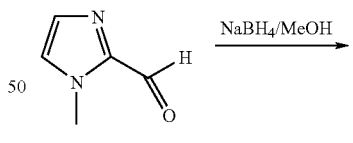

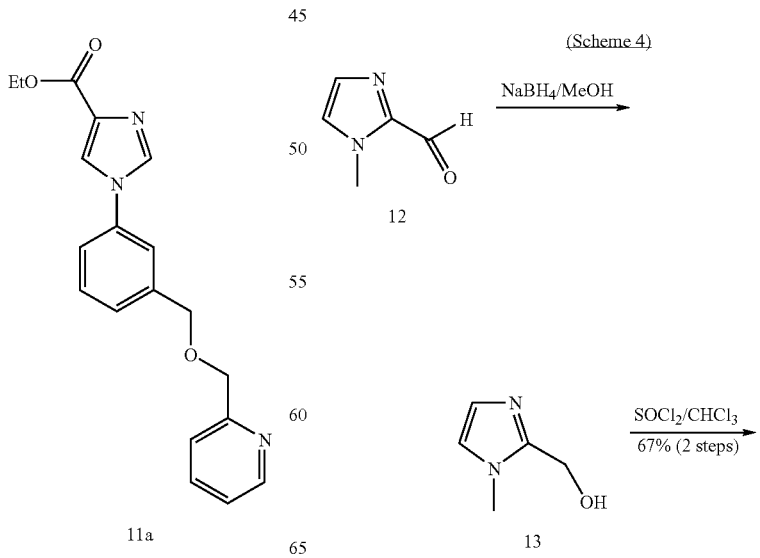

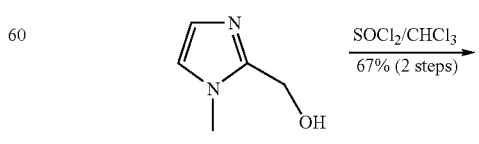

-continued

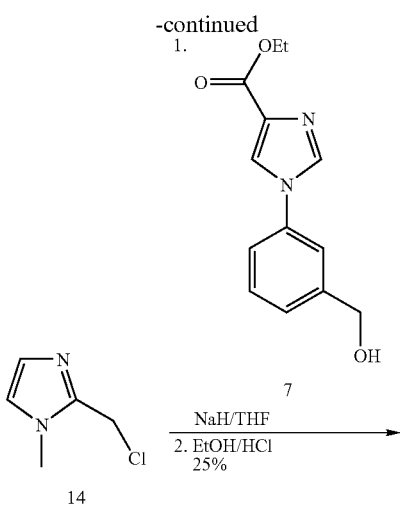

[(1-Methyl-1H-imidazol-2-yl)-methanol] (13)

To a solution of 1-methyl-2-imidazole carbaldehyde (12) (500 mg, 4.5 mmol) in methanol (5 mL) at 0° C. was added sodium borohydride (85 mg, 2.2 mmol) portion wise and stirred for 30 min. Reaction was followed by TLC and was quenched by adding acetone at 0° C. The reaction mixture was diluted with water and ethylacetate.

The compound 13 (510 mg) was isolated as white solid along with inorganic impurity after concentration of aqueous layer.

[2-Chloromethyl-1-methyl-1H-imidazole] (14)

To a solution of compound 13 (250 mg, 2.23 mmol) in chloroform (5 mL) was added thionyl chloride (500 mg, 4.20 mmol) and refluxed for 3 h. The reaction mixture was allowed to come to room temperature and concentrated. The reaction mixture was diluted with diethyl ether (30 mL) and concentrated. The crude product 14 (200 mg, 67%) was characterized by GC-MS and it was used as such for the next step.

[1-[3-(1-Methyl-1H-imidazol-2-ylmethoxymethyl)-phenyl]-1H-imidazole-4-carboxylic acid ethyl ester] (14a)

To a suspension of NaH (308 mg, 7.7 mmol, 60% in mineral oil) in dry THF (6 mL) under $N_2$ atmosphere was added a solution of alcohol 7 (410 mg, 1.38 mmol) in THF (2 mL) while stirring for 30 min at room temperature. The reaction mixture was cooled to 0° C. and the compound 14 (crude 200 mg, 1.53 mmol) in THF (1 mL) was added dropwise and allowed to come to room temperature during a period of 30 min after which it was refluxed for 12 h. The mixture was quenched with ice water (5 mL), acidified to pH 2-3 by adding aqueous HCl solution (2N). The reaction mixture was extracted with $CH_2Cl_2$ (3×20 mL), washed with brine, dried over $Na_2SO_4$ and concentrated. The crude mass was taken in ethanol (10 mL), purged HCl gas for 30 min. and stirred at room temperature for 3 h. After evaporation of solvent, the crude mass was purified by column chromatography using 28% ethylacetate in hexane to furnish 14a (150 mg, 25%) as a white solid, mp-83.8-88.6° C.

Example 5

The synthesis of compounds 16 and 17 is shown in Scheme 5:

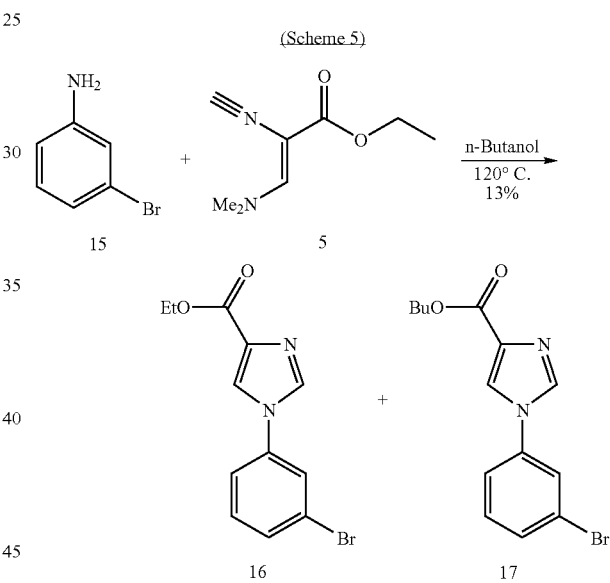

[1-(3-Bromo-phenyl)-1H-imidazole-4-carboxylic acid ethyl ester] (16) and [1-(3-Bromo-phenyl)-1H-imidazole-4-carboxylic acid n-butyl ester] (17)

A solution of compound 5 (11.8 g, 79 mmol) and 3-bromo aniline (15) (11.3 g, 65 mmol) in n-butanol (90 mL) was heated to reflux for 72 h [reaction was monitored by TLC]. Reaction mixture was concentrated under reduced pressure to remove n-butanol and the residue was passed through silica gel column, eluated with a mixture of ethyl acetate and hexane to give a mixture of ethyl and n-butyl ester compounds which was then separated by flash column chromatography over silica gel using 3:7 mixture ethyl acetate and hexane as eluant. Finally the ethyl ester was further purified by crystallization to furnish 16 (2.5 g, 13%) as brown solid and n-butyl ester 17 (500 mg) as a brown liquid.

Example 6

The synthesis of compounds 18 and 19 is shown in Scheme 6:

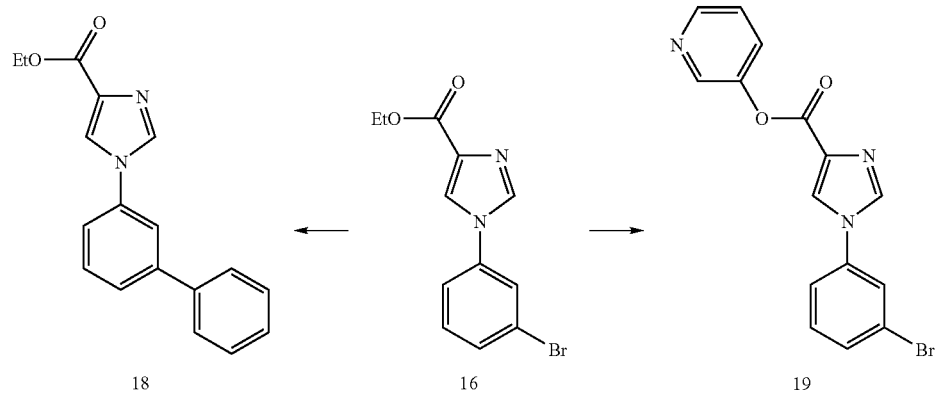

[1-Biphenyl-3-yl-1H-imidazole-4-carboxylic acid ethyl ester hydrochloride] (18)

A solution of 16 (150 mg, 0.51 mmol), phenylboronic acid (68 mg, 0.56 mmol) and $Na_2CO_3$ (162 mg, 1.53 mmol) in $DME/H_2O$ 4:1 (6 mL) was thoroughly purged with argon, after which $Pd(PPh_3)_2Cl_2$ (36 mg; 0.05 mmol) was added and the mixture was heated to 110° C. for 16 h. The solvents were removed in vacuo and the residue was purified on combiflash sq16 (4 g kisel gel column; eluant: 100% Benzine (bp=80-100° C.) to 100% EtOAc)). The solvent was evaporated to dryness, redissolved in diethyl ether and precipitated by adding 2.8M HCl (diethyl ether) to afford 94 mg (63%) 18 as a white solid. HRMS (ESI$^+$): m/z=292.3364 [M+H]

1-[3-(6-Fluoro-pyridin-3-yl)-phenyl]-1H-imidazole-4-carboxylic acid ethyl ester (19)

The compound was synthesised in analogy with 18 using 2-fluoropyridinyl-5-boronic acid. HRMS (ESI$^+$): m/z=311.3146 [M+H]

Example 7

The synthesis of compounds 20-22 is shown in Scheme 7:

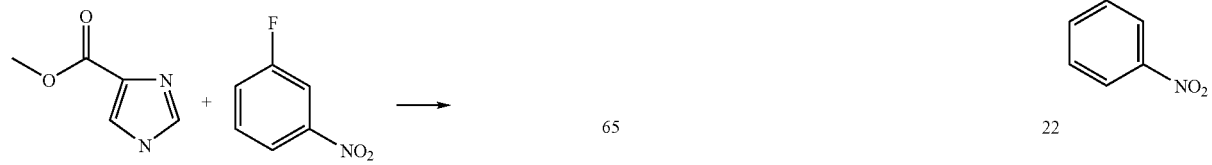

[1-(3-Nitro-phenyl)-1H-imidazole-4-carboxylic acid methyl ester] (20)

1H-Imidazole-4-carboxylic acid methyl ester (1 g, 7.9 mmol) was dissolved in MeOH and NaH (348 mg, 8.7 mmol) was added slowly. When the gas evolution had ceased 1-fluoro-3-nitro benzene (926 uL, 8.7 mmol) was added, and the mixture was heated to 150° C. under $N_2$ for 16 h. After cooling to room temperature the precipitation was isolated by suction filtration, washed with MeOH, and dried under vacuum to afford 1.3 g (67%) of 20. HRMS (ESI$^+$): m/z=247.2091 [M+H]

[1-(3-Nitro-phenyl)-1H-imidazole-4-carboxylic acid] (21)

1-(3-Nitro-phenyl)-1H-imidazole-4-carboxylic acid methyl ester 20 (0.7 g; 2.8 mmol) was suspended in MeOH (15 mL) and 2N NaOH aq. (2 mL) was added. The mixture was stirred at 70° C. for 16 h. The MeOH was evaporated and the product was isolated by suction filtration, washed with water and dried under vacuum to afford 0.56 g (86%) of 21 as an off-white solid. HRMS (ESI$^+$): m/z=233.1823 [M+H]

[1-(3-Nitro-phenyl)-1H-imidazole-4-carboxylic acid pyridin-3-yl ester] (22)

1-(3-Nitro-phenyl)-1H-imidazole-4-carboxylic acid 21 (0.1 g, 0.4 mmol) was suspended in $CH_2Cl_2$ (5 mL) and a drop of DMF (cat.) was added. Then oxalyl chloride (111 μL, 1.29 mmol) was added and the reaction mixture was stirred at room temperature for 1 h. The organic layer was removed by decantation and the remaining solid was washed twice with $CH_2Cl_2$. The solid was suspended in $CH_2Cl_2$ and 3-hydroxypyridine was added dropwise. The clear solution was stirred at room temperature for 2 h after which 1N NaOH (aq) was added and the layers were separated. Concentration of the organic layer followed by column chromatography on silica gel with 5% MeOH in $CH_2Cl_2$ afforded 14 mg (10%) of 22 as a white solid. HRMS (ESI$^+$): m/z=310.268 [M+H]

[1-(3-Bromo-phenyl)-4H-imidazole-4-carboxylic acid pyridin-3-yl ester]

The compound was prepared in analogy with 22 using 1-(3-Bromo-phenyl)-1H-imidazole-4-carboxylic acid. HRMS (ESI$^+$): m/z=344.167 [M+H]

Example 8

The synthesis of compounds 23a-m and 24a-m is shown in Scheme 8

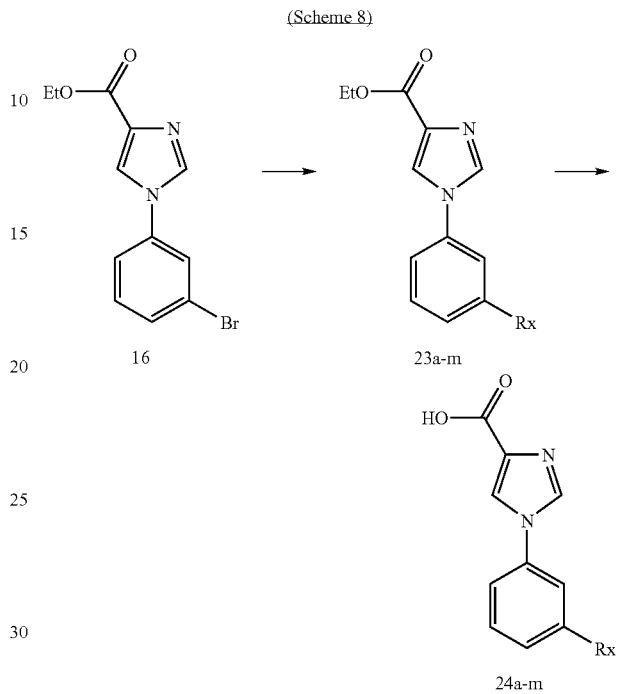

(Scheme 8)

1-Biphenyl-3-yl-1H-imidazole-4-carboxylic acid ethyl ester (23a)

This compound was synthesised as compound 18.

1-(5'-Fluoro-2'-methoxy-biphenyl-3-yl)-1H-imidazole-4-carboxylic acid ethyl ester (23b)

This compound is synthesised in analogy with 18 using 16 and 5-fluoro-2-methoxyphenylboronic acid.

1-(2'-Methoxy-biphenyl-3-yl)-1H-imidazole-4-carboxylic acid ethyl ester (23c)

This compound is synthesised in analogy with 18 using 16 and 2-methoxyphenylboronic acid.

1-(2'-Cyano-biphenyl-3-yl)-1H-imidazole-4-carboxylic acid ethyl ester (23d)

This compound is synthesised in analogy with 18 using 16 and 2-cyanophenylboronic acid.

1-(Z-Chloro-biphenyl-3-yl)-1H-imidazole-4-carboxylic acid ethyl ester (23e)

This compound is synthesised in analogy with 18 using 16 and 2-chlorophenylboronic acid.

1-(2'-Trifluoromethoxy-biphenyl-3-yl)-1H-imidazole-4-carboxylic acid ethyl ester (23f)

This compound is synthesised in analogy with 18 using 16 and 2-(trifluoromethoxy)phenyl-boronic acid.

1-(6'-Fluoro-2'-methoxy-biphenyl-3-yl)-1H-imidazole-4-carboxylic acid ethyl ester (23g)

This compound is synthesised in analogy with 18 using 16 and 6-fluoro-2-methoxyphenylboronic acid.

1-(3'-Fluoro-2'-methoxy-biphenyl-3-yl)-1H-imidazole-4-carboxylic acid ethyl ester (23h)

This compound is synthesised in analogy with 18 using 16 and 3-fluoro-2-methoxyphenylboronic acid.

1-[3-(2-Fluoro-pyridin-3-yl)-phenyl]-1H-imidazole-4-carboxylic acid ethyl ester (23I)

This compound is synthesised in analogy with 18 using 16 and 2-fluoro-3-pyridylboronic acid.

1-[3-(2,4-Difluoro-pyridin-3-yl)-phenyl]-1H-imidazole-4-carboxylic acid ethyl ester (23j)

This compound is synthesised in analogy with 18 using 16 and 2,4-difluoro-3-pyridylboronic acid.

1-[3-(2-Fluoro-pyridin-4-yl)-phenyl]-1H-imidazole-4-carboxylic acid ethyl ester (23k)

This compound is synthesised in analogy with 18 using 16 and 2-fluoro-4-pyridylboronic acid.

1-[3-(2-Chloro-pyridin-3-yl)-phenyl]-1H-imidazole-4-carboxylic acid ethyl ester (23l)

This compound is synthesised in analogy with 18 using 16 and 2-chloro-3-pyridylboronic acid.

1-[3-(2,4-Dimethoxy-pyrimidin-5-yl)-phenyl]-1H-imidazole-4-carboxylic acid ethyl ester (23m)

This compound is synthesised in analogy with 18 using 16 and 2,4-dimethoxy-5-pyrimidylboronic acid.

1-Biphenyl-3-yl-1H-imidazole-4-carboxylic acid (24a)

This compound was prepared by hydrolysis of 23a using a 1:1 mixture of aqueous potassium hydroxide (2M) and ethanol.

1-(5'-Fluoro-2'-methoxy-biphenyl-3-yl)-1H-imidazole-4-carboxylic acid (24b)

This compound was prepared by hydrolysis of 23b using a 1:1 mixture of aqueous potassium hydroxide (2M) and ethanol.

1-(2'-Methoxy-biphenyl-3-yl)-1H-imidazole-4-carboxylic acid (24c)

This compound is prepared by hydrolysis of 23c using a 1:1 mixture of aqueous potassium hydroxide (2M) and ethanol.

1-(2'-Cyano-biphenyl-3-yl)-1H-imidazole-4-carboxylic acid (24d)

This compound is prepared by hydrolysis of 23d using a 1:1 mixture of aqueous potassium hydroxide (2M) and ethanol.

1-(2'-Chloro-biphenyl-3-yl)-1H-imidazole-4-carboxylic acid (24e)

This compound is prepared by hydrolysis of 23e using a 1:1 mixture of aqueous potassium hydroxide (2M) and ethanol.

1-(2'-Trifluoromethoxy-biphenyl-3-yl)-1H-imidazole-4-carboxylic acid (24f)

This compound is prepared by hydrolysis of 23f using a 1:1 mixture of aqueous potassium hydroxide (2M) and ethanol.

1-(6'-Fluoro-2'-methoxy-biphenyl-3-yl)-1H-imidazole-4-carboxylic acid (24g)

This compound is prepared by hydrolysis of 23g using a 1:1 mixture of aqueous potassium hydroxide (2M) and ethanol.

1-(3'-Fluoro-2'-methoxy-biphenyl-3-yl)-1H-imidazole-4-carboxylic acid (24h)

This compound is prepared by hydrolysis of 23h using a 1:1 mixture of aqueous potassium hydroxide (2M) and ethanol.

1-[3-(2-Fluoro-pyridin-3-yl)-phenyl]-1H-imidazole-4-carboxylic acid (24i)

This compound is prepared by hydrolysis of 23i using a 1:1 mixture of aqueous potassium hydroxide (2M) and ethanol.

1-[3-(2,4-Difluoro-pyridin-3-yl)-phenyl]-1H-imidazole-4-carboxylic acid (24j)

This compound is prepared by hydrolysis of 23j using a 1:1 mixture of aqueous potassium hydroxide (2M) and ethanol.

1-[3-(2-Fluoro-pyridin-4-yl)-phenyl]-1H-imidazole-4-carboxylic acid (24k)

This compound is prepared by hydrolysis of 23k using a 1:1 mixture of aqueous potassium hydroxide (2M) and ethanol.

1-[3-(2-Chloro-pyridin-3-yl)-phenyl]-1H-imidazole-4-carboxylic acid (24l)

This compound is prepared by hydrolysis of 23l using a 1:1 mixture of aqueous potassium hydroxide (2M) and ethanol.

1-[3-(2,4-Dimethoxy-pyrimidin-5-yl)-phenyl]-1H-imidazole-4-carboxylic acid (24m)

This compound is prepared by hydrolysis of 23m using a 1:1 mixture of aqueous potassium hydroxide (2M) and ethanol.

Test Methods

In Vitro Inhibition of $^3$H-Flunitrazepam ($^3$H—FNM) Binding

The GABA recognition site and the benzodiazepine modulatory unit can selectively be labelled with $^3$H-flunitrazepam.
Tissue Preparation Preparations are performed at 0-4° C. unless otherwise indicated. Cerebral cortex from male Wistar rats (150-200 g) is homogenised for 5-10 sec in 20 ml Tris-HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 µl of test solution and 25 µl of $^3$H—FNM (1 nM, final concentration), mixed and incubated for 40 min at 2° C. Non-specific binding is determined using Clonazepam (1 µM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results 25-75% inhibition of specific binding must be obtained, before calculation of an $IC_{50}$.

The test value will be given as $IC_{50}$ (the concentration (µM) of the test substance which inhibits the specific binding of $^3$H—FNM by 50%).

$$IC_{50} = \text{(applied test substance concentration, µM)} \times \frac{1}{\left(\frac{C_o}{C_x} - 1\right)}$$

where $C_o$ is specific binding in control assays, and $C_x$ is the specific binding in the test assay.

(The calculations assume normal mass-action kinetics).

Test results from these experiments with a number of compounds of the invention are shown in Table 1 below.

TABLE 1

| Test compound | In vitro binding $IC_{50}$ (µM) |
|---|---|
| Compound 11a | 0.024 |
| Compound 16 | 0.024 |
| Compound 20 | 0.18 |

The invention claimed is:

1. A compound of the general formula (I):

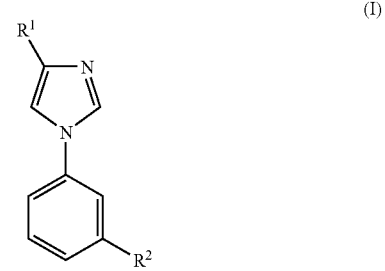

any of its stereoisomers or any mixture of its stereoisomers, or a pharmaceutically acceptable salt thereof, wherein $R^1$ represents —COOR$^3$;

wherein $R^3$ represents hydrogen, alkyl, cycloalkyl, cycloalkylakyl, alkenyl, alkynyl, aryl or heteroaryl;

which aryl or heteroaryl group is optionally substituted with one or more substituents independently selected from the group consisting of:

halo, hydroxy, $R^aR^bN$—, $R^aR^bN$-alkyl, cyano, nitro, trifluoromethyl, trifluoromethoxy, alkoxy, cycloalkoxy, $R^a$—(C=O)—, $R^a$—O—(C=O)—, alkyl, cycloalkyl, cycloalkylalkyl, alkenyl, and alkynyl;

wherein $R^a$ and $R^b$ independent of each other are hydrogen or alkyl;

$R^2$ represents halo, nitro, $R^c$— or $R^c$—(CH$_2$)$_m$—O—(CH$_2$)$_n$—;

wherein m is 0 or 1; n is 0 or 1; and $R^c$ is an aryl or heteroaryl group;

which aryl or heteroaryl group is optionally substituted with one or more substituents independently selected from the group consisting of:

halo, hydroxy, $R^dR^eN$—, $R^dR^eN$-alkyl, $R^dR^eN$—(C=O)—, cyano, nitro, trifluoromethyl, trifluoromethoxy, alkoxy, cycloalkoxy, $R^d$—(C=O)—, $R^d$—O—(C=O)—, alkyl, cycloalkyl, cycloalkylalkyl, alkenyl, and alkynyl;

wherein when both m and n are 0, $R^c$ is not phenyl or pyridinyl; and wherein $R^d$ and $R^e$ independent of each other are hydrogen or alkyl with the provisos that when $R^3$ represents hydrogen, $R^2$ is not halo; and when $R^3$ represents alkyl, $R^2$ is not nitro or halo.

2. The compound of claim 1, or a pharmaceutically acceptable salt thereof, wherein $R^1$ represents —COOR$^3$; wherein $R^3$ represents hydrogen or alkyl.

3. The compound of claim 1, or a pharmaceutically acceptable salt thereof, wherein $R^1$ represents —COOR$^3$; wherein $R^3$ represents heteroaryl.

4. The compound of claim 1, or a pharmaceutically acceptable salt thereof, wherein $R^2$ represents halo or nitro.

5. The compound of claim 1, or a pharmaceutically acceptable salt thereof, wherein $R^2$ represents $R^c$— or $R^c$—(CH$_2$)$_m$—O—(CH$_2$)$_n$—;

wherein m is 0 or 1; n is 0 or 1; and $R^c$ is an aryl or heteroaryl group;

which aryl or heteroaryl group is optionally substituted with one or more substituents independently selected from the group consisting of:

halo, hydroxy, $R^dR^eN$—, $R^dR^eN$-alkyl, $R^dR^eN$—(C=O)—, cyano, nitro, trifluoromethyl, trifluoromethoxy, alkoxy, cycloalkoxy, $R^d$—(C=O)—, $R^d$—O—(C=O)—, alkyl, cycloalkyl, cycloalkylalkyl, alkenyl, and alkynyl;

wherein $R^d$ and $R^e$ independent of each other are hydrogen or alkyl.

6. A compound selected from the group consisting of:
1-[3-(Pyridin-2-ylmethoxymethyl)-phenyl]-1H-imidazole-4-carboxylic acid ethyl ester;
1-[3-(1-Methyl-1H-imidazol-2-ylmethoxymethyl)-phenyl]-1H-imidazole-4-carboxylic acid ethyl ester;
1-Biphenyl-3-yl-1H-imidazole-4-carboxylic acid ethyl ester;
1-[3-(6-Fluoro-pyridin-3-yl)-phenyl]-1H-imidazole-4-carboxylic acid ethyl ester;
1-(3-Nitro-phenyl)-1H-imidazole-4-carboxylic acid;
1-(3-Nitro-phenyl)-1H-imidazole-4-carboxylic acid pyridin-3-yl ester;
1-(3-Bromo-phenyl)-1H-imidazole-4-carboxylic acid pyridin-3-yl ester;
1-(5'-Fluoro-2'-methoxy-biphenyl-3-yl)-1H-imidazole-4-carboxylic acid ethyl ester;
1-(T-Methoxy-biphenyl-3-yl)-1H-imidazole-4-carboxylic acid ethyl ester;
1-(2'-Cyano-biphenyl-3-yl)-1H-imidazole-4-carboxylic acid ethyl ester;
1-(2'-Chloro-biphenyl-3-yl)-1H-imidazole-4-carboxylic acid ethyl ester;
1-(2'-Trifluoromethoxy-biphenyl-3-yl)-1H-imidazole-4-carboxylic acid ethyl ester;
1-(6'-Fluoro-2'-methoxy-biphenyl-3-yl)-1H-imidazole-4-carboxylic acid ethyl ester;
1-(3'-Fluoro-2'-methoxy-biphenyl-3-yl)-1H-imidazole-4-carboxylic acid ethyl ester;
1-[3-(2-Fluoro-pyridin-3-yl)-phenyl]-1H-imidazole-4-carboxylic acid ethyl ester;
1-[3-(2,4-Difluoro-pyridin-3-yl)-phenyl]-1H-imidazole-4-carboxylic acid ethyl ester;
1-[3-(2-Fluoro-pyridin-4-yl)-phenyl]-1H-imidazole-4-carboxylic acid ethyl ester;
1-[3-(2-Chloro-pyridin-3-yl)-phenyl]-1H-imidazole-4-carboxylic acid ethyl ester;
1-[3-(2,4-Dimethoxy-pyrimidin-5-yl)-phenyl]-1H-imidazole-4-carboxylic acid ethyl ester;
1-Biphenyl-3-yl-1H-imidazole-4-carboxylic acid;
1-(5'-Fluoro-2'-methoxy-biphenyl-3-yl)-1H-imidazole-4-carboxylic acid;
1-(T-Methoxy-biphenyl-3-yl)-1H-imidazole-4-carboxylic acid;
1-(T-Cyano-biphenyl-3-yl)-1H-imidazole-4-carboxylic acid;
1-(2'-Chloro-biphenyl-3-yl)-1H-imidazole-4-carboxylic acid;
1-(T-Trifluoromethoxy-biphenyl-3-yl)-1H-imidazole-4-carboxylic acid;
1-(6'-Fluoro-2'-methoxy-biphenyl-3-yl)-1H-imidazole-4-carboxylic acid;
1-(3'-Fluoro-2'-methoxy-biphenyl-3-yl)-1H-imidazole-4-carboxylic acid;
1-[3-(2-Fluoro-pyridin-3-yl)-phenyl]-1H-imidazole-4-carboxylic acid;
1-[3-(2,4-Difluoro-pyridin-3-ye-phenyl]-1H-imidazole-4-carboxylic acid;
1-[3-(2-Fluoro-pyridin-4-yl)-phenyl]-1H-imidazole-4-carboxylic acid;
1-[3-(2-Chloro-pyridin-3-yl)-phenyl]-1H-imidazole-4-carboxylic acid;
1-[3-(2,4-Dimethoxy-pyrimidin-5-yl)-phenyl]-1H-imidazole-4-carboxylic acid;
stereoisomers and mixtures of stereoisomers thereof;
or a pharmaceutically acceptable salt thereof.

7. A pharmaceutical composition, comprising a therapeutically effective amount of a compound of claim 1, any of its stereoisomers or any mixture of its stereoisomers, or a pharmaceutically acceptable salt thereof, together with at least one pharmaceutically acceptable carrier, excipient or diluent.

* * * * *